United States Patent
Rutz et al.

(10) Patent No.: US 10,173,357 B2
(45) Date of Patent: Jan. 8, 2019

(54) POLY(ETHYLENE GLYCOL) CROSS-LINKING OF SOFT MATERIALS TO TAILOR VISCOELASTIC PROPERTIES FOR BIOPRINTING

(71) Applicant: Northwestern University, Evanston, IL (US)

(72) Inventors: Alexandra L. Rutz, Chicago, IL (US); Ramille N. Shah, Hinsdale, IL (US)

(73) Assignee: Northwestern University, Evanston, IL (US)

(*) Notice: Subject to any disclaimer, the term of this patent is extended or adjusted under 35 U.S.C. 154(b) by 1038 days.

(21) Appl. No.: 14/497,274

(22) Filed: Sep. 25, 2014

(65) Prior Publication Data
US 2015/0084232 A1   Mar. 26, 2015

Related U.S. Application Data

(60) Provisional application No. 61/882,811, filed on Sep. 26, 2013.

(51) Int. Cl.
*B29C 47/00* (2006.01)
*A61L 27/44* (2006.01)
(Continued)

(52) U.S. Cl.
CPC .......... *B29C 47/0004* (2013.01); *A61L 27/18* (2013.01); *A61L 27/38* (2013.01); *A61L 27/44* (2013.01); *A61L 27/52* (2013.01); *A61L 27/56* (2013.01); *C12N 5/0068* (2013.01); *B29K 2889/00* (2013.01); *C12M 33/00* (2013.01); *C12N 2537/00* (2013.01); *C12N 2537/10* (2013.01)

(58) Field of Classification Search
CPC ...... B29C 47/0004; A61L 27/18; A61L 27/38; A61L 27/44; A61L 27/52; A61L 27/56
USPC ....................................... 264/211.24
See application file for complete search history.

(56) References Cited

U.S. PATENT DOCUMENTS

| | | |
|---|---|---|
| 5,162,430 A | 11/1992 | Rhee et al. |
| 6,384,105 B1 | 5/2002 | He et al. |

(Continued)

FOREIGN PATENT DOCUMENTS

| | | |
|---|---|---|
| WO | WO2007120840 | 10/2007 |
| WO | WO2010030964 | 3/2010 |
| WO | WO2011073991 | 6/2011 |

OTHER PUBLICATIONS

Skardal et al."Bioprinting vessel-like constructs using hyaluronan hydrogels crosslinked with tetrahedral polyethylene glycol tetracrylates", May 23, 2010, Biomaterials 31.*

(Continued)

*Primary Examiner* — Christina A Johnson
*Assistant Examiner* — Xue Liu
(74) *Attorney, Agent, or Firm* — Bell & Manning, LLC

(57) ABSTRACT

Extrudable hydrogel compositions for printing 3D objects, such as cell growth scaffolds, are provided. Also provided are methods for making the crosslinked hydrogel compositions and the printed objects and methods for culturing cells using the cell growth scaffolds. The hydrogel precursor solutions are aqueous solutions comprising a biocompatible polymer, functionalized polyethylene glycol as a crosslinker and, optionally, cells and/or bioactive factors.

20 Claims, 9 Drawing Sheets

(51) Int. Cl.
  *A61L 27/38* (2006.01)
  *A61L 27/18* (2006.01)
  *A61L 27/52* (2006.01)
  *A61L 27/56* (2006.01)
  *C12N 5/00* (2006.01)
  *C12M 1/26* (2006.01)

(56) References Cited

U.S. PATENT DOCUMENTS

| | | |
|---|---|---|
| 6,602,952 B1 | 8/2003 | Bentley et al. |
| 7,368,484 B2 | 5/2008 | Levy |
| 7,714,088 B2 | 5/2010 | Harris et al. |
| 8,207,353 B2 | 6/2012 | Sill et al. |
| 2009/0117087 A1 | 5/2009 | Carroll et al. |
| 2011/0313542 A1 | 12/2011 | Forgacs et al. |
| 2012/0238644 A1* | 9/2012 | Gong .............. A61K 9/06 514/781 |
| 2012/0258068 A1* | 10/2012 | Seliktar ........ A61K 47/48215 424/78.17 |
| 2012/0270810 A1* | 10/2012 | Preiss-Bloom ...... A61L 24/08 514/21.2 |

OTHER PUBLICATIONS

International Search Report and Written Opinion for Intl. Pat. Appl. No. PCT/US2014/057558, dated Dec. 17, 2014.

Cohen et al., Direct Freeform Fabrication of Seeded Hydrogels in Arbitrary Geometries, Tissue Engineering, vol. 12, No. 5, 2006, pp. 1325-1335.

Skardal et al., Bioprinting vessel-like constructs using hyaluronan hydrogels crosslinked with tetrahedral polyethylene glycol tetracrylates, Biomaterials, vol. 31, May 23, 2010, pp. 6173-6181.

Skardal et al., Photocrosslinkable Hyaluronan-Gelatin Hydrogels for Two-Step Bioprinting, Tissue Engineering: Part A, vol. 16, No. 8, 2010, pp. 2675-2685.

Chan et al., Robust and Semi-Interpenetrating Hydrogels from Poly(ethylene glycol) and Collagen for Elastomeric Tissue Scaffolds, Macromolecular Bioscience, vol. 12, Oct. 15, 2012, pp. 1490-1501.

Dikovsky et al., The effect of structural alterations of PEG-fibrinogen hydrogel scaffolds on 3-D cellular morphology and cellular migration, Biomaterials, vol. 27, Oct. 21, 2005, pp. 1496-1506.

Singh et al., Capillary morphogenesis in PEG-collagen hydrogels, Biomaterials, vol. 34, Sep. 7, 2013, pp. 9331-9340.

Rutz et al., A Cross-linking Technique for Rapid Prototyping of 3D Micropatterned Cell-Laden Hydrogels, Abstract for presentation at the Annual Meeting of the Biomedical Engineering Society, May 2013.

Rutz et al., A Cross-linking Technique for Rapid Prototyping of 3D Micropatterned Cell-Laden Hydrogels, Presentation at the Annual Meeting of the Biomedical Engineering Society, Sep. 27, 2013.

\* cited by examiner

Table 1

| Formulation | Increasing Gelatin Concentration | | | | Increasing PEG:Gelatin (m:m) | | |
|---|---|---|---|---|---|---|---|
| | 2% gelatin 0.2 PEG:gelatin | 3% gelatin 0.2 PEG:gelatin | 4% gelatin 0.2 PEG:gelatin | 5% gelatin 0.2 PEG:gelatin | 5% gelatin 0.1 PEG:gelatin | 5% gelatin 0.2 PEG:gelatin | 5% gelatin 0.3 PEG:gelatin |
| G'-G" cross-over [minutes] | 84 ± 22 | 23 ± 9 | 28 ± 6 | 15 ± 8 | 30 ± 6 | 15 ± 8 | 22 ± 4 |
| G'$_{2hrs}$ [Pa] | 1.21 ± 1.01 | 62.7 ± 7.14 | 157 ± 41.1 | 554 ± 258 | 37.4 ± 1.96 | 554 ± 258 | 589 ± 219 |
| δ$_{2hrs}$ [°] | 29.8 ± 11.9 | 0.72 ± 0.14 | 0.73 ± 0.17 | 0.28 ± 0.12 | 2.73 ± 0.10 | 0.28 ± 0.12 | 1.13 ± 1.35 |
| γ$_c$ [%] | 2200 ± 537 | 1000 ± 0 | 794 ± 0 | 461 ± 193 | 1587 ± 5.77 | 461 ± 193 | 378 ± 107 |
| G'$_c$ [Pa] | 7.53 ± 6.08 | 213 ± 29.5 | 403 ± 89.1 | 791 ± 277 | 115 ± 16.3 | 791 ± 277 | 868 ± 50.3 |
| σ$_c$ [Pa] | 144 ± 78.6 | 2130 ± 295 | 3197 ± 708 | 3407 ± 1329 | 1815 ± 254 | 3407 ± 1329 | 3295 ± 1014 |

FIG. 9

POLY(ETHYLENE GLYCOL) CROSS-LINKING OF SOFT MATERIALS TO TAILOR VISCOELASTIC PROPERTIES FOR BIOPRINTING

CROSS-REFERENCE TO RELATED APPLICATIONS

The present application claims priority to U.S. Provisional Patent Application No. 61/882,811 that was filed Sep. 26, 2013, the entire contents of which are hereby incorporated by reference.

BACKGROUND

Three dimensional printing of cell-laden hydrogels is of interest for tissue engineering due to the ability to create pre-seeded three dimensional (3D) structures with defined shape and internal geometry. However, hydrogel 3D printing is challenged by the fact that most hydrogel precursors are solutions that cannot form self-supporting structures. In addition, bioink development often presents a struggle between achieving printability and achieving biological compatibility. Conventional bioinks of hydrogel precursor solutions possess low viscosities and are conventionally cross-linked to form a gel either during or after the printing process. Post-printing cross-linking results in a printed layer lacking definition and resolution since solutions often diffuse rapidly after extrusion. Furthermore, crosslinking solutions post-printing is incompatible with printing multi-layer structures.

To overcome the poor structural definition of solution phase bioinks, researchers have attempted a few strategies including increasing polymer concentration, co-printing with a high shape fidelity support ink and layer-by-layer cross-linking; yet, these strategies have limitations. For example, relatively high polymer weight fractions (>5 wt %) can inhibit encapsulated cell spreading, migration, proliferation, and consequently tissue formation. In the case of co-printing with non-sacrificial support inks, the support ink may have mechanical properties ideal for maintaining shape and stability, but these may not be optimal for soft, non-load bearing tissues. The third strategy, layer-by-layer cross-linking, must occur extremely rapid to yield defined strands, yet too rapid cross-linking can result in nozzle clogging and poor inter-layer adhesion. Furthermore, co-printing multiple materials that utilize different solidification mechanisms, such as ionic, ultraviolet, chemical, or temperature-induced cross-linking, may not be feasible using layer-by-layer cross-linking.

Unlike solution phase bioinks, gel phase bioinks have been rarely explored. (See A. Skardal, J. Zhang, G. D. Prestwich, *Biomaterials* 2010, 31, 6173; D. L. Cohen. E. Malone. H. Lipson, L. J. Bonassar, *Tissue Eng.* 2006, 12, 1325; and A. Skardal, J. Zhang, L. McCoard, X. Xu, S. Oottamasathien, G. D. Prestwich, *Tissue Eng. Part A* 2010, 16, 2675.) Practical, efficient, functional, and multi-material bioprinting has yet to be reported with gel phase bioinks.

SUMMARY

Hydrogel precursor solutions and extrudable compositions comprising crosslinked hydrogels for printing 3D objects, such as cell growth scaffolds, are provided. Also provided are methods for making the crosslinked hydrogel compositions and the printed objects and methods for culturing cells and growing tissues using the cell growth scaffolds.

One embodiment of a method for forming a three-dimensional object comprises the steps of extruding a hydrogel composition having a shear storage modulus of less than 300 Pa through the annulus of a channel, the hydrogel composition comprising: water; a crosslinked biocompatible polymer; and a bioactive factor, cells or a combination thereof, wherein the crosslinks between the biocompatible polymer chains comprise repeating units having the following structure:

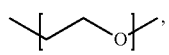

to form a strand comprising a continuous matrix of the biocompatible polymer, wherein the strand substantially retains the three-dimensional shape imparted to it by the extrusion.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 9. Table 1 showing a rheology summary of bioink formulations. Mean and standard deviation displayed, N=3. Values taken from time and first amplitude sweeps.

DETAILED DESCRIPTION

Figure 1:
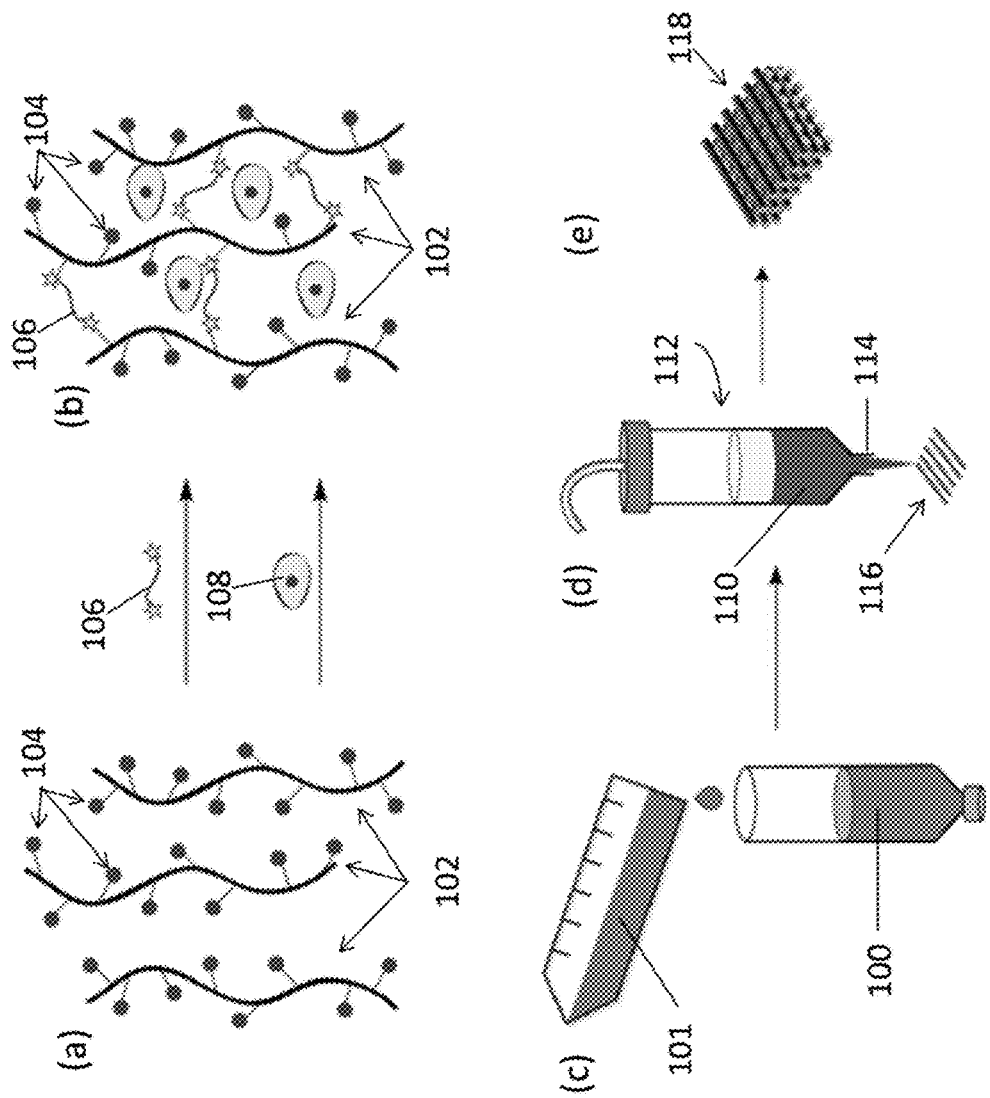
FIG. 1. A schematic diagram of a method for formulating and printing a cell-loaded hydrogel composition.

Hydrogel precursor solutions and extrudable compositions comprising crosslinked hydrogels for printing 3D objects, such as cell growth scaffolds are provided. Also provided are methods for making the crosslinked hydrogels and the printed objects and methods for culturing cells using the cell growth scaffolds.

The hydrogel precursor solutions are aqueous solutions comprising a biocompatible polymer, functionalized polyethylene glycol as a crosslinker and, optionally, cells and/or a bioactive factor and/or a crosslinking initiator. The polymer solutions alone (that is—before the addition of the cross-linker) can have low viscosities (~1 to 1000 cP), but upon addition of the cross-linker and subsequent crosslinking reaction, a self-supporting hydrogel material is formed.

The extrudable hydrogel compositions are formed via the gelation of the biocompatible polymer as the result of crosslinking. The transition from solution to gel phase from cross-linking renders them self-supporting. Self-supporting structures formed by the extrusion of the hydrogel compositions are characterized in that they substantially retain the 3D shape imparted to them by the extrusion process and do not require a supporting structure or matrix to maintain their shape and structural integrity. This property of the hydrogel compositions makes it possible to fabricate porous 3D structures in a layer-by-layer printing process. Because the hydrogel gelling is nearly complete at the time of extrusion, unwanted changes in rheological properties during the extrusion process are avoided.

The biocompatible polymer of the precursor solutions and the hydrogel compositions can be a naturally occurring or synthetic polymer and may be a biopolymer or a non-biological organic polymer. For the purposes of this disclosure, a biocompatible polymer is a polymer that does not have a significant negative impact on cell viability or tissue growth and viability and does not induce a negative reaction, such as a chronic immune response or inflammatory response in a patient into which it is implanted. Thus, biocompatible polymers are suitable components for cell culturing and/or tissue growth substrates. Examples of polymers that can be included in the precursor solutions include polymers of amino acids, such as polypeptides and proteins, and saccharides.

The PEG crosslinkers are well-suited for cell culturing applications because PEG is biocompatible with a wide variety of cells. The functionalized PEG crosslinkers may be linear or branched. In some embodiments of the precursor solutions and hydrogel compositions, the functionalized PEG crosslinkers are homobifunctional linear PEG molecules. However, heteropolyfunctional (e.g., hbeterobifunctional linear) PEG molecules can also be used. The functionalized PEG crosslinkers comprise a PEG-based spacer chain with pendant functional groups and/or end functional groups attached to the spacer chain. The pendant- and/or end functional groups are capable of undergoing crosslinking reactions with functional groups on the biocompatible polymers to form covalent bonds. These crosslinking reactions result in the formation of a hydrogel in which the polymer chains are crosslinked by the PEG. As such, the crosslinks between the biocompatible polymer chains comprise repeating units of the following structure:

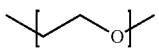

The number of repeating units will vary depending upon the desired properties of the inks, which can be tailored by adjusting the molecular weight of the crosslinker. By way of illustration only, in some embodiments the crosslinks have the structure:

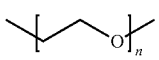

where n is at least three. This includes embodiments in which n is at least five. For example, in some embodiments n is in the range from about 10 to about 200. However, crosslinks with n values outside of this range can also be used.

In some embodiments, the PEG is the only crosslinker of the biocompatible polymers in the hydrogels. In other embodiments, co-crosslinkers can be present, although PEG is desirably the majority crosslinker, with co-crosslinkers present at minor concentrations (e.g., less than 20 wt. %, less than 10 wt. %, less than 5 wt. % or less than 1 wt. % based on the total weight of crosslinker). In some embodiments, the precursor solutions and hydrogels are free of high viscosity polymer solutions, such as concentrated polymer solutions (for example, those with polymer concentrations of greater than 5 wt. %) or inherently viscous polymer solutions (that is, solutions that have high viscosities even at low polymer concentrations). This includes embodiments in which the precursor solutions and hydrogels are free of hyaluronic acid (HA).

The functional groups of the PEG can be selected to be reactive with the functional groups of the specific biocompatible polymer used. Potential crosslinking chemistries that can be used include reactions between amines and carboxylic acids, acrylates and acrylates, acrylates and thiols, aldehydes and amines, azides and alkynes. For example, a thiol-containing material may utilize a maleimide derived PEG, a vinyl sulfone derived PEG, or an acrylate derived PEG. By way of illustration, the PEG crosslinkers may comprises a PEG-based spacer chain with maleimide or N-hydroxy-succinimide ester groups on either end.

By changing the molecular weight, number and/or type of crosslinkable functional groups, molecular structure (linear or branched) and concentration of the PEG, the properties of the hydrogel precursor solutions and the hydrogels can be tailored for specific printing systems and selected printing parameters.

Biological cells can be incorporated directly into the hydrogel precursor solutions and encapsulated in the extruded hydrogels that are made from the hydrogel precursor solutions, thereby providing the capacity to form cell-loaded 3D structures via extrusion processes. Alternatively, the biological cells can be put onto the hydrogels after the extrusion. Examples of biological cells that can be incorporated into the hydrogel precursor solutions and the extruded hydrogels, or placed onto the extruded hydrogels, include tissue-forming cells and cells that are precursors to tissue-forming cells. Human mesenchymal stem cells, hematopoetic stem cells, embryonic stem cells, and induced pluripotent stem cells are examples of precursors to tissue-forming cells. Examples of tissue-forming cells include osteoblasts, chondrocytes, fibroblasts, endothelial cells, and myocytes.

Bioactive factors that can be included in the hydrogel precursor solutions and/or the hydrogel compositions are substances that promote the growth of tissues from cells in structures made from the hydrogel compositions. Examples of bioactive factors include genes, proteins, peptides, growth factors, pharmaceutical compounds, antibiotics and the like that facilitate tissue growth, by, for example, inducing cell differentiation. Although the bioactive factors may be polymers (e.g., proteins and peptides), they are a distinct component from the biocompatible polymer and they do not provide a continuous matrix in structures formed from the extruded bioinks. In some embodiments, the bioactive factors are covalently bound to the crosslinks between the biocompatible polymer chains. This can be accomplished by using heterofunctional, multi-arm (>2) polyethylene glycol crosslinkers having a first set of functional groups that react with the biocompatible polymer pre-extrusion to form the hydrogel composition and a second set of functional groups that react with the bioactive factors to form covalent bonds.

The general approach to formulating extrudable hydrogel compositions is to screen various concentrations of the chosen PEG cross-linker(s) with a solution of the biocompatible polymer. This polymer solution may also contain cells or bioactive agents prior to the addition of a concentrated PEG cross-linker solution. From this screening, soft gels hydrogel compositions that can be extruded through needles are candidates for printing.

The hydrogels are characterized as having a shear storage modulus (G') that is much greater than their shear loss modulus (G"). The lightly crosslinked extrudable hydrogels can also be characterized by their shear storage modulus at the time the viscoelastic properties have stabilize ($G'_{stable}$), which should be sufficiently low to allow the hydrogels to be extruded through narrow-diameter channels, yet high enough to allow the extruded hydrogels to be self-supporting and retain their shape after printing. By way of illustration, some embodiments of the extrudable hydrogels have a $G'_{stable}$ of 300 Pa or lower. This includes embodiments having a $G'_{stable}$ of 250 or lower. For example, the extrudable hydrogels can have a $G'_{stable}$ in the range from about 1 to about 200 Pa. This includes embodiments of the extrudable hydrogels having a $G'_{stable}$ in the range from about 50 to about 150 Pa. For example the extrudable hydrogels may have a $G'_{stable}$ in the range from about 90 to about 150 Pa. $G'_{stable}$ can be measured using a shear stress sweep test according the methods described in the Examples.

The amount of biocompatible polymer in the precursor solutions needed to achieve hydrogel compositions having suitable viscoelastic properties for extrusion will depend on the nature of the biocompatible polymer and the molecular weight of and number of crosslinking functional groups on the PEG crosslinker. The biocompatible polymer is present in sufficient quantities to provide a continuous matrix in structures formed by the extrusion of the crosslinked hydrogel compositions. However, the biocompatible polymer may be present is relatively low quantities, such that the viscosity of the solution comprising the biocompatible polymer is close to or equal to that of water at a given temperature prior to the onset of crosslinking. By way of illustration only, in some embodiments of the crosslinked hydrogel compositions the biocompatible polymer is present at concentrations in the range from about 1% to about 10% w/v. This includes embodiments of the crosslinked hydrogel compositions that comprise biocompatible polymer in the range from about 1% to about 5% w/v. Again, by way of illustration only, the viscosities of the polymer solutions before addition of the cross-linker can be in the range from about 1 to about 1000 cP at temperature in the range from about 20 to about 40° C.

The optimal mass ratio for the PEG crosslinker and biocompatible polymer will also depend on the molecular weight and number of crosslinking functional groups on the PEG. By way of illustration only, in some embodiments of the hydrogel precursor solutions and hydrogel compositions, the mass ratio of PEG crosslinker to biocompatible polymer is in the range from about 0.1 to about 1 and the weight average molecular weight (Mw) of the PEG crosslinker is in the range from about 0.5 to about 6 k.

Three dimensional objects can be formed from the crosslinked hydrogel compositions by extruding the hydrogel compositions through the annulus of a channel. The extrusion may be by way of printing, that is, extrusion through the annulus of a printhead nozzle. However, extrusion may be carried out through other annular channels, such as needles and capillary tubes, as well.

FIG. 1 is a schematic diagram illustrating the printing process. As shown in panel (a), the process begins with a starting solution 100 comprising water, and a biocompatible polymer 102 having a plurality of reactive functional groups 104. A second solution 101 comprising functionalized PEG crosslinker 106, along with any biological cells 108 to be included, is added to starting solution 100, as shown in panel (c). The resulting solution is transferred to a vessel 112, such as a printhead, having an extrusion orifice 114 (panel (d)) and exposed to conditions that promote crosslinking reactions between biocompatible polymer 102 and functionalized PEG crosslinker 106 to provide a lightly crosslinked hydrogel composition 110 or "bioink", as illustrated in panel (b). The crosslinking can be, for example, photocrosslinking, thermal crosslinking, or ionic crosslinking and may be carried out with or without the aid of an initiator. Once the crosslinking has proceeded to a point where the viscoelastic properties of hydrogel composition 110 have stabilized, it is extruded in a series of strands 116 (panel (d)). Thus, the extent of crosslinking should not be so high that the hydrogel will not yield to shear stress and will not be extrudable. The hydrogel composition may be extruded through a nozzle by application of a movable piston, pneumatic or mechanically driven. This extrusion can be used to build a 3D structure 118 in a layer-by-layer process (panel (e)). The layer-by-layer deposition of fibers can be used to form 3D-objects with overall architectures previously defined through computer aided design (CAD) drawings and internal architecture designed using 3D-printer specific software. This printing method is direct and achieves well-defined micro-scale patterning.

In some embodiments of the printing process, the hydrogel precursor solution is converted into the crosslinked hydrogel composition within a printing cartridge. In these embodiments, aqueous solutions of the biocompatible polymer, PEG crosslinkers (linear or branched), and cells and/or bioactive factors (optional) are mixed together thoroughly and loaded into a printing cartridge. In the printing cartridge, crosslinking occurs to such a degree as to gel the solution, as described above.

Where biological cells and/or bioactive factors are present in the extruded hydrogel composition, extrusion is desirably carried out at temperatures that are not greater than physiological temperatures. For example, extrusion (e.g., printing) may be carried out at temperature in the range from about 20° C. to about 40° C. Also, for cell culturing and tissue growth applications, it may be desirable to form a highly porous structure with small feature dimensions. Therefore, in some embodiments of the extrusion process an annulus (e.g., printing nozzle diameter) of 500 μm or smaller may be employed. This includes embodiments in which the annulus is 200 μm or smaller.

Optionally, a secondary cross-linking procedure can be performed post-printing to further stabilize and tailor the mechanical properties of the fabricated 3D multi-layer structures. The additional crosslinking reactions between the PEG crosslinkers and the biocompatible polymer can occur (or be induced to occur using, for example heat or radiation, such as UV radiation) after extrusion in order to further solidify the extruded structure. Where secondary crosslinking is used, the biocompatible polymer may comprise two different sets of reactive functional groups, wherein a first set of the functional groups reacts with the functionalized PEG crosslinker pre-extrusion to form the hydrogel composition and a second set of functional groups reacts to form crosslinks post-extrusion. The post-extrusion crosslinks can be formed by direct reactions between the second set of functional groups or through an additional crosslinking agent. Gelatin methacrylate is an example of a biocompatible polymer that can undergo post-extrusion. secondary crosslinking. Gelatin methacrylate comprises both amine and acrylate functional groups. Therefore, the amine groups can react with a N-hydroxysuccinimide (NHS) functionalized PEG crosslinker pre-extrusion to form the hydrogel composition. Then, after the hydrogel is extruded into an object, the hydrogel can be exposed to ultraviolet radiation to crosslink acrylate groups that are still present on the gelatin.

Alternatively, the secondary crosslinks can be formed by post-extrusion reactions between unreacted functional groups on the functionalized polyethylene glycol crosslinker and unreacted functional groups on the biocompatible polymer. This can be accomplished by using heterofunctional, multi-arm (>2) polyethylene glycol crosslinkers having a first set of functional groups that react with the biocompatible polymer pre-extrusion to form the hydrogel composition and a second set of functional groups that react with the biocompatible polymer after hydrogel extrusion to form secondary crosslinks that stabilize the structure. A functionalized polyethylene glycol crosslinker comprising both NHS groups and acrylate groups is an example of a heterofunctional multi-arm crosslinker that can undergo post-extrustion, secondary crosslinking. During hydrogel formation, the NHS groups present on the crosslinker can react with the react with and crosslink the biocompatible polymer chains. Then, after the hydrogel is extruded into an object the hydrogel can be exposed to ultraviolet radiation to crosslink acrylate groups that are still present on the crosslinker.

Figure 2:
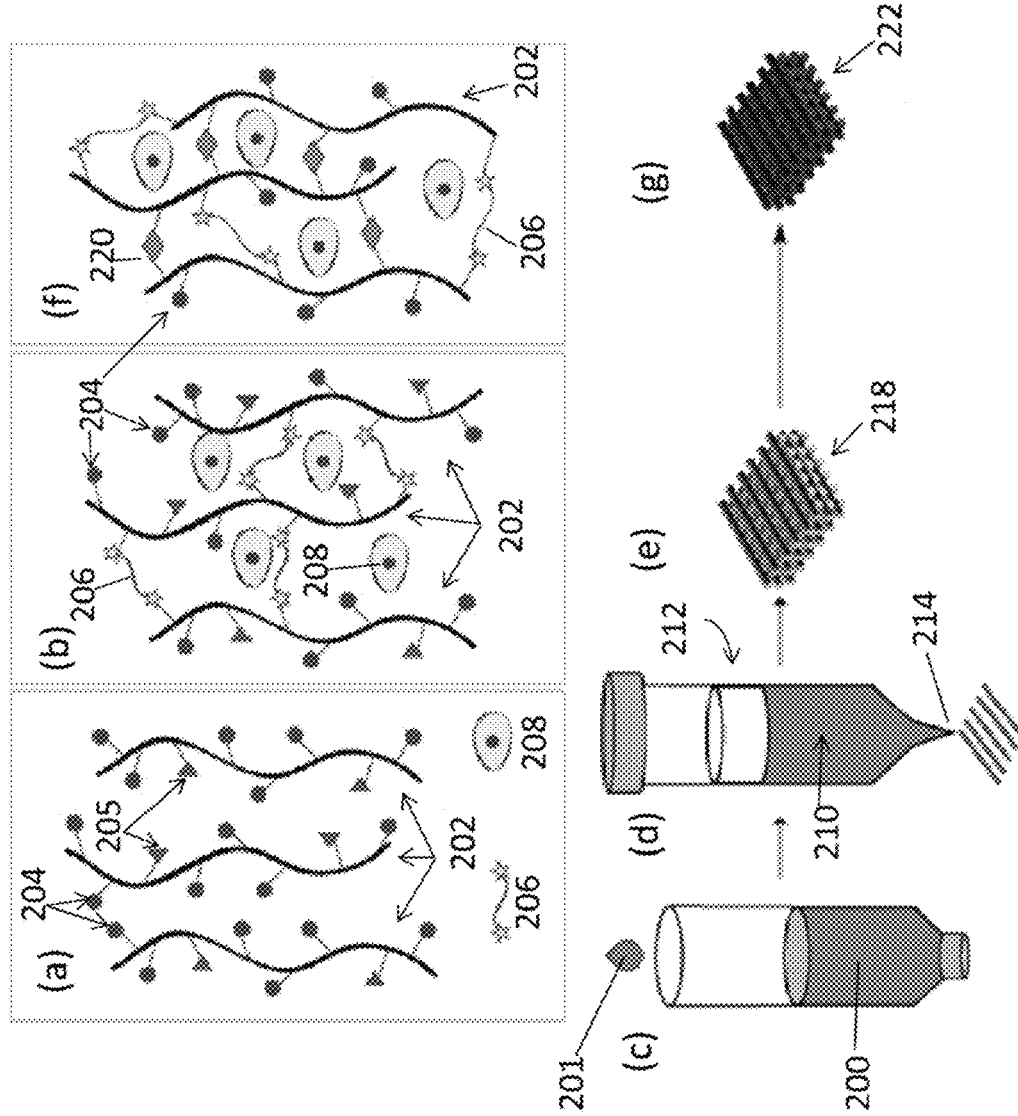
FIG. 2. A schematic diagram of a method for formulating and printing a cell-loaded hydrogel composition, including a secondary crosslinking step.

The use of a secondary cross-linking procedure is illustrated schematically in FIG. 2. A shown in panel (a), the process begins with a starting solution 200 comprising water, and a biocompatible polymer 202 having a plurality of first reactive functional groups 204 and a plurality of second reactive functional groups 205. A second solution 201 comprising functionalized PEG crosslinker 206, along with any biological cells 208 to be included, is added to starting solution 200, as shown in panel (c). The resulting solution is transferred to a vessel 212, such as a printhead, having an extrusion orifice 214 (panel (d)) and exposed to conditions that promote crosslinking reactions between biocompatible polymer 202 and reactive functional groups 204 on functionalized PEG crosslinker 206 to provide a lightly crosslinked hydrogel composition 210 or "bioink", as illustrated in panel (b). Once the crosslinking has proceeded to a point where the viscoelastic properties of hydrogel composition 210 have stabilized, it is extruded in a series of strands 216 (panel (d)). The extrusion can be used to build a 3D structure 218 in a layer-by-layer process (panel (e)). Reactive functional groups 205 can then be exposed to conditions that promote secondary crosslinks 220 to form, as illustrated in panel (f). The secondary crosslinking can be, for example, photocrosslinking, thermal crosslinking, or ionic crosslinking and may be carried out with or without the aid of an initiator. The result is a mechanically robust, heavily crosslinked 3D structure 222 (panel (g)).

The crosslinked hydrogel compositions can be extruded into intricate, free-standing and self-supporting 3D structures. The 3D structures may be simple structures, such as cylinder-like structures that are obtained by printing the crosslinked hydrogel compositions in a line, or beads that are obtained by printing individual strands of the crosslinked hydrogel compositions. More complex, multilayered 3D structures, such as grids, can be obtained by printing the crosslinked hydrogel compositions in a layer-by-layer process. Because the hydrogels can be extruded through channels having extremely narrow diameters, they can be used to print strands with correspondingly fine diameters. Thus, 3D strands printed using the hydrogels may have dimensions of 500 µm or smaller, 300 µm or smaller and 200 µm or smaller.

Porous scaffolds for culturing cells and growing tissues are examples of the types of 3D structures that can be fabricated using the present hydrogel compositions. As illustrated in the examples, below, these scaffolds can provide excellent cell viability even after cross-linking and printing and can be mechanically robust enough for surgical implantation. The scaffolds are porous structures that permit cell integration, tissue ingrowth, and vascularization. The use of 3D printing for the fabrication of the scaffolds is advantageous because it provides for regular geometric patterning of the layers that make up the scaffold, which makes it possible to control and tailor the porosity, pore size and pore interconnectivity of the scaffold. The printing can be carried out at, near, or below physiological temperatures (~37° C.) to promote cell viability when cells are encapsulated in the hydrogel composition to be printed.

EXAMPLES

Figure 3:
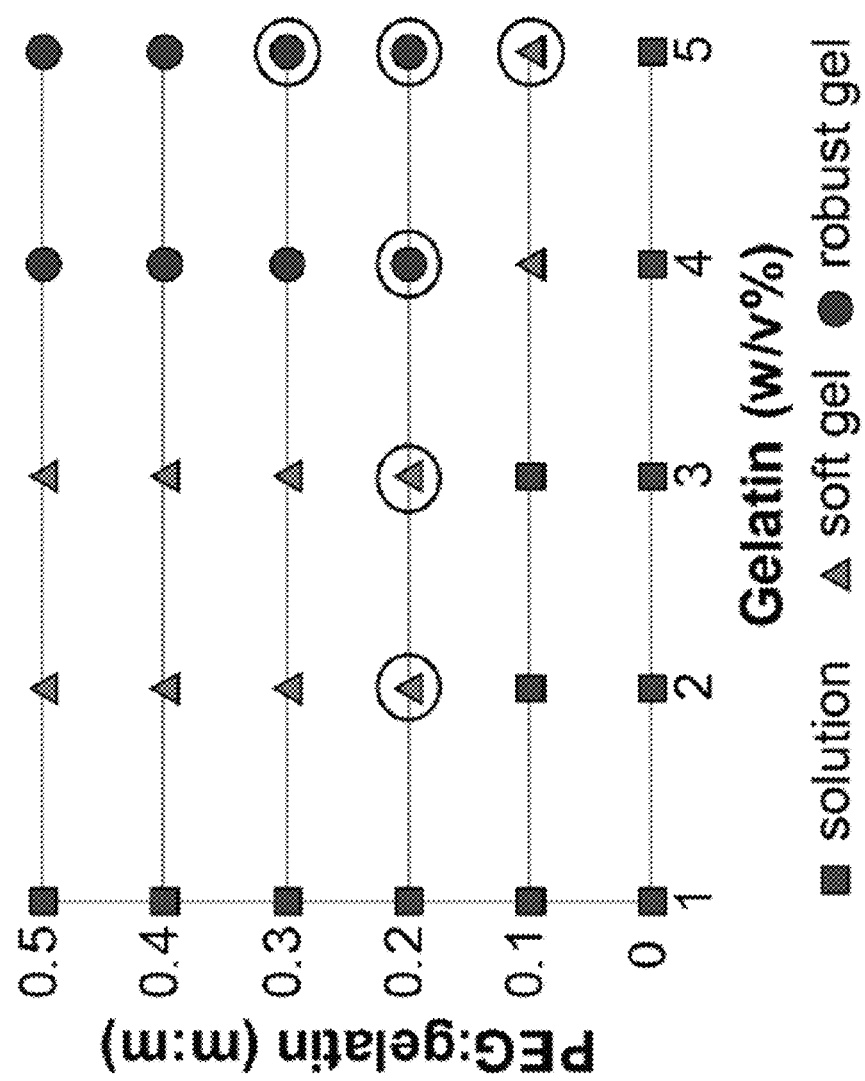
FIG. 3. Phase plot of varying gelatin concentrations with varying PEG:gelatin (m:m) ratios, circled formulas were rheologically tested.

These examples demonstrate bioinks that meet many criteria for both printing and biological compatibility. The bioinks were gelled prior to extrusion. Gels behave as solids and thus do not flow. However, the results reported here show that when the cross-linking is carefully controlled, gel bioinks can be extruded through fine diameter nozzles (200 µm) while maintaining their structural integrity. The examples also illustrate properties of the gels that make them printable through rheological studies. Additionally, the reported method shows significant promise for being applied to many materials. Extrusion was carried out using hydrogel precursor solutions that were lightly cross-linked with a long length chemical cross-linker, a homobifunctional polyethylene glycol (PEG) ending in two activated ester groups (succinimidyl valerate: SVA), which readily react with free amines (FIG. 2). PEG is a widely accepted biomaterial with FDA-approved uses. Gelatin, a heterogeneous mixture of polypeptides derived from collagen, was chosen for these studies since it is abundant in amines and biologically-recognized peptide sequences (i.e. for cell binding and enzyme degradation), and is also biocompatible. When the PEG cross-linker was added in small proportions to warmed gelatin solutions, gels of a soft, spreadable consistency were formed and were found to be extrudable. The capacity to tune gel properties by varying the polymer (gelatin) concentration of the precursor solution was investigated. Polymer concentration influences material properties (i.e. modulus and degradation) and thus, also influences tissue formation. For encapsulating cells, relatively low polymer weight fractions (<5 wt %) were preferred to promote nutrient diffusion and permit cell spreading and migration. Phase plots were created by screening varying polymer concentrations against varying PEG:gelatin mass to mass (m:m) ratios (FIG. 3). Mixtures of each formula were prepared and incubated at 37° C. for 120 minutes. Material "phase", solution or gel behavior, was determined by tube inversion. A qualitative test of gel consistency was also performed by manipulating the gels with a spatula. Gels that spread without fracturing were designated "soft" and those retaining their shape and not able to be spread were designated "robust". In extrusion tests, soft gels ejected as smooth strands of gel, which are desired for printing, and therefore, soft gels were identified as candidate bioinks. Robust gels either were unable to be extruded or required significant pressure, producing inconsistent strands at very slow mass flow rates, both of which are non-ideal for printing. At the selected PEG ratios of up to 0.5, soft gels formed at 2, 3, 4, and 5 w/v % gelatin at and close to the minimum PEG ratio that induced gelation. Importantly, controlling polymer concentration illustrates the ability to tune material properties and biological response.

For future development of bioinks, studies were conducted to associate ink properties with printability in order to both promote more informed design of new inks and assure quality of existing inks. The degree of cross-linking was investigated in all formulas to determine if soft gels exhibited a common degree of cross-linking. The 2,4,6-Trinitrobenzenesulfonic acid (TNBS) assay was used to determine the amount of free amines after gelation. Soft gels in all gelatin concentrations had a percentage of reacted amines in the range from 25-45%. As the polymer fraction decreased, a larger PEG ratio was required for gelation to occur. As well, the percent of reacted amines increased in gels formed at the minimum PEG ratio as the polymer concentration decreased. Gels were not observed in 1 w/v % gelatin at any ratio despite showing reaction with the PEG cross-linker. It is believed that as the polymer solution became more dilute, there was an increase in the amount of PEG cross-linker that was connected to polymer at only one reacted end (dangling end) or PEG cross-linker with both ends reacted on the same polymer chain, therefore these reactions do not result in functional cross-links for gelation (i.e. not contribute to a continuous gel network). Because of this varying degree of functional reactivity across all gelatin concentrations, some formulations that resulted in solutions or robust gels also had percent reacted amines within the range associated with soft, printable gels (25-45%).

Figure 4:
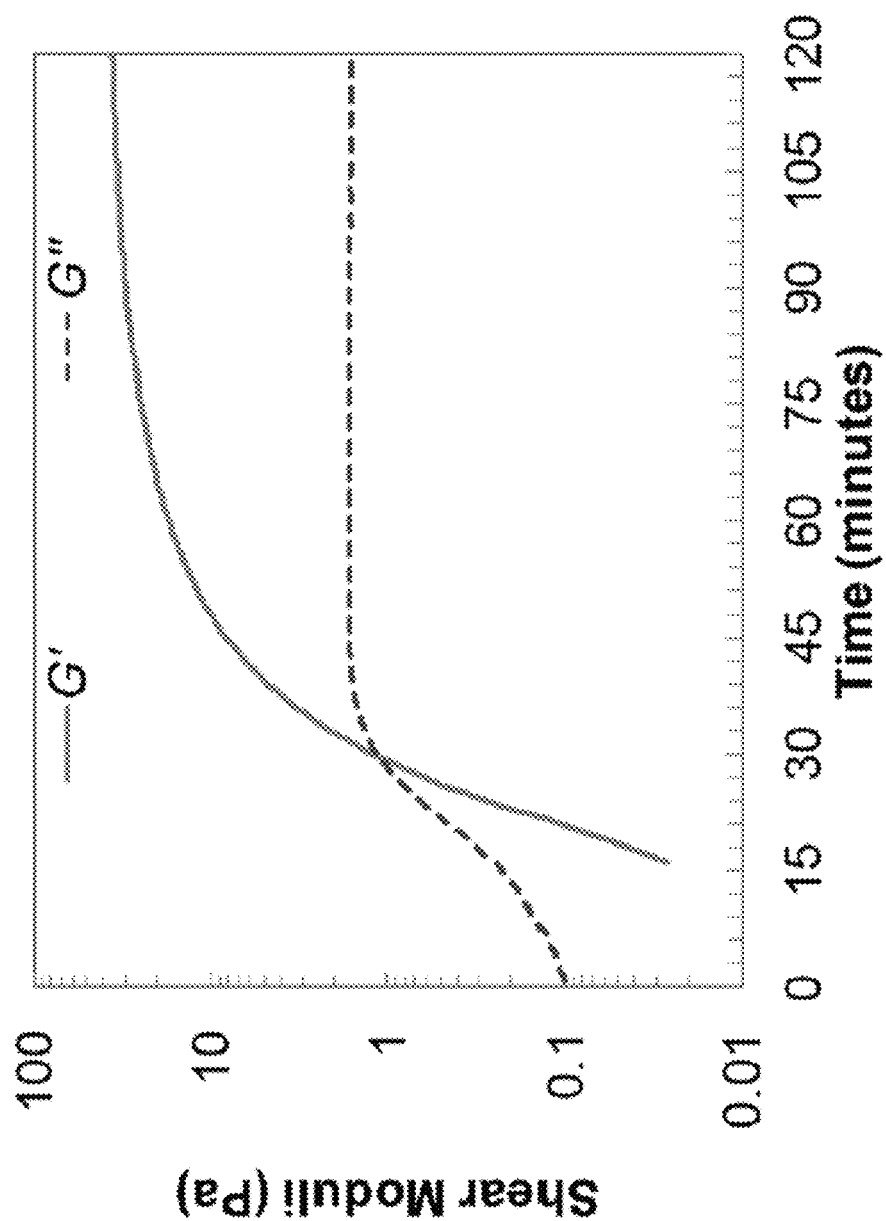
FIG. 4. Graph of the gelation profile of 5 w/v % gelatin and 0.1 PEG:gelatin (m:m) after addition of PEG cross-linker.
Figure 5:
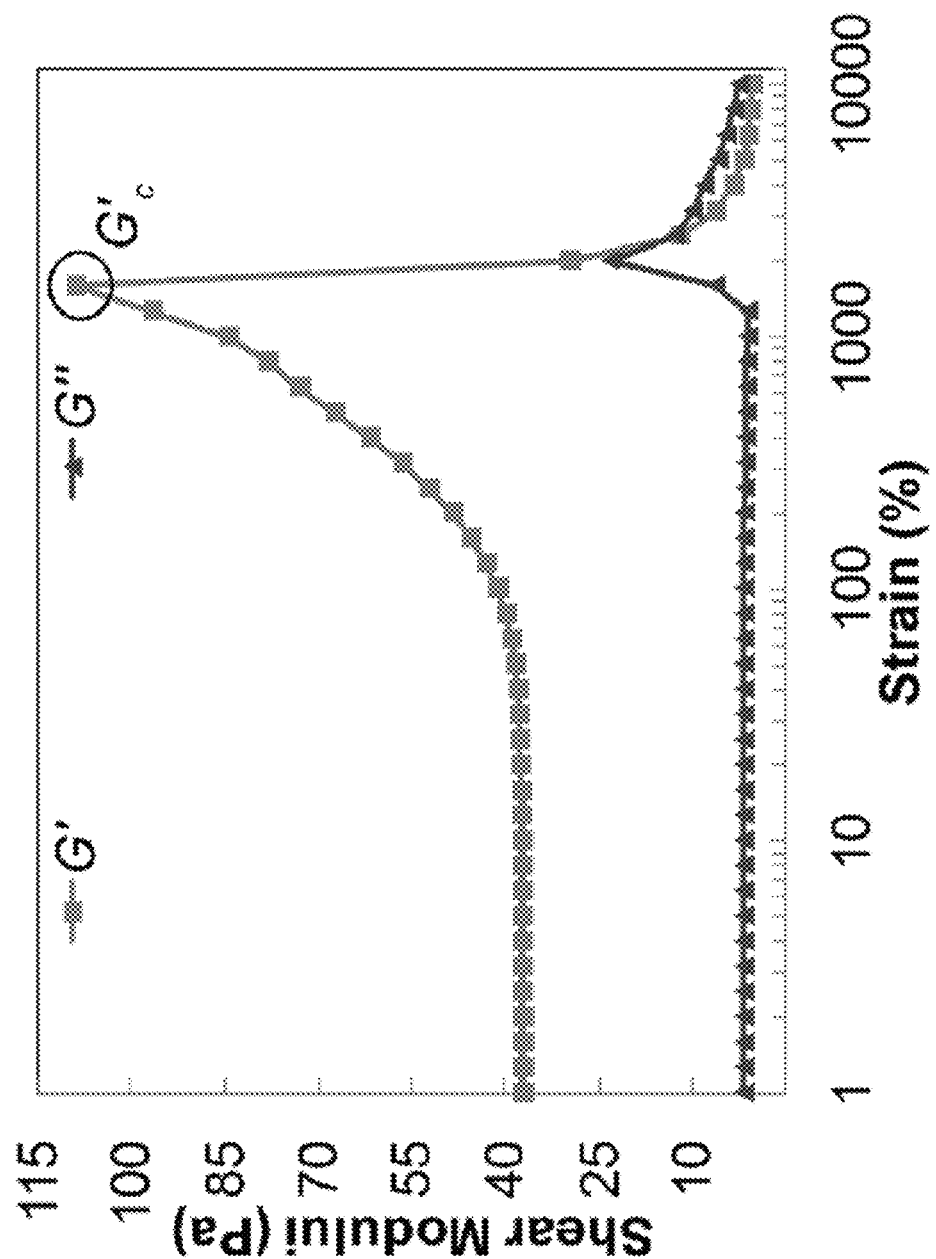
FIG. 5. Graph of the response of 5 w/v % gelatin and 0.1 PEG:gelatin (m:m) to increasing strains, failure ($G'_c$) at 1590% strain.

To further probe properties associated with the printability of soft gels, several PEG cross-linked formulations (circled in FIG. 3) were tested rheologically to explore mechanical variables. Most rheological characterization of bioinks focus on viscosity. Since these bioinks were gels, other types of tests were necessary. Alter loading a warmed, freshly prepared formulation into the rheometer, an oscillatory time sweep (1% strain, 10 rad/s angular frequency) was performed for 120 minutes at 37° C., followed by a frequency sweep at 1% strain to confirm expected gel viscoelasticity (G'~independent of frequency and G'>>G"), and two strain sweeps at 10 rad/s. A table summarizing key results is shown in Table 1 of FIG. 9. Gelation (G'–G" cross-over, FIG. 4) of both soft and robust gel formulas typically occurred between 15 and 30 minutes. An exception was the formulation consisting of 2 w/v % gelatin and 0.2 PEG ratio, which gelled at ~80 minutes; this sample lies barely within the gel regime (FIG. 3), yielding only a marginal gel network. Storage moduli were mostly stable by 120 min; however, in most formulations, G' continued to show modest growth over longer times. During 3D printing of these soft gel formulations over the course of several hours, no drastic changes in printing parameters (i.e. extrusion pressure), however, were needed. It is important to note that in the few studies published on near-gel (G'≈G") or gel phase bioinks, these gels were printed within a very narrow window of time immediately after addition of a cross-linker and before substantial gelation had occurred. (See, A. Skardal, J. Zhang, G. D. Prestwich, Biomaterials 2010, 31, 6173; D. L. Cohen, E. Malone, H. Lipson, L. J. Bonassar, Tissue Eng. 2006, 12, 1325 and A. Skardal, J. Zhang, L. McCoard, X. Xu, S. Oottamasathien, G. D. Prestwich, Tissue Eng. Part A 2010, 16, 2675.) The present methods overcome such impracticality since the degree of cross-linking is controlled by fine additions of cross-linker, and printing occurs when cross-linking, and therefore G', have stabilized. After 120 minutes, soft gel formulas possessed mean storage moduli ($G'_{2\ hrs}$) ranging from ~1-100 Pa and robust gels over 150 Pa. In the first strain sweep, gels exhibited a linear response at strains up to ~50%; after 50%, they exhibited strain-hardening until catastrophic yielding. Soft gels yielded at remarkably high strains ($\gamma_c \geq 1000\%$; FIG. 5) while robust gels yielded at lower strains, less than 800%. Storage modulus ($G'_{2\ hrs}$), critical storage modulus ($G'_c$), and critical stress ($\sigma_c$) increased while critical strain ($\gamma_c$) decreased when the polymer concentration increased at a fixed PEG ratio or when the PEG ratio increased at a fixed polymer concentration (Table 1 of FIG. 9). Repeated amplitude sweeps showed that samples suffered catastrophic failure at the critical yielding point. Such extensive damage, however, was not observed following extrusion. In extrusion, shear stress is maximized at the nozzle walls, in contrast to rheological testing where stress is experienced homogeneously throughout the sample. Extrusion may be facilitated by localized yielding/rupture at the nozzle surface when the wall shear stress ($\sigma_{wall}$) exceeds the critical stress ($\sigma_c$) necessary to induce yielding. An estimate of the magnitude of wall shear stress may be made based on a highly simplified assumption that the full pressure drop driving ink printing ($\Delta P$) is applied only over the capillary extrusion nozzle of radius R and length L, (Equation 1):

$$\sigma_{wall} = \Delta P \cdot R / (2L) \qquad \text{Equation 1}$$

Using parameters relevant for the printing conditions used here ($\Delta P = 1.5 \times 10^5$ Pa, R=0.1 mm, L=2 mm), $\sigma_{wall}$ is estimated to be 3750 Pa, which is of the same order of magnitude as the stresses at which yielding occurs in these gels in rheological testing (Table 1 of FIG. 9). With higher critical stresses than soft gels, robust gels may not be capable of yielding under such printing conditions. Conversely, the soft gel PEG cross-linked bioinks remained intact and extruded as continuous, cohesive filaments, an important requirement for 3D printing. These PEG cross-linked gelatin gels manage to stay cohesive even when subjected to the enormous stretching associated with flowing from the printing cartridge barrel through a tiny capillary. The printed gel filaments displayed elastic behavior under uniaxial loads which may contribute to their ability to retain cohesiveness under severe deformation.

Figure 6:
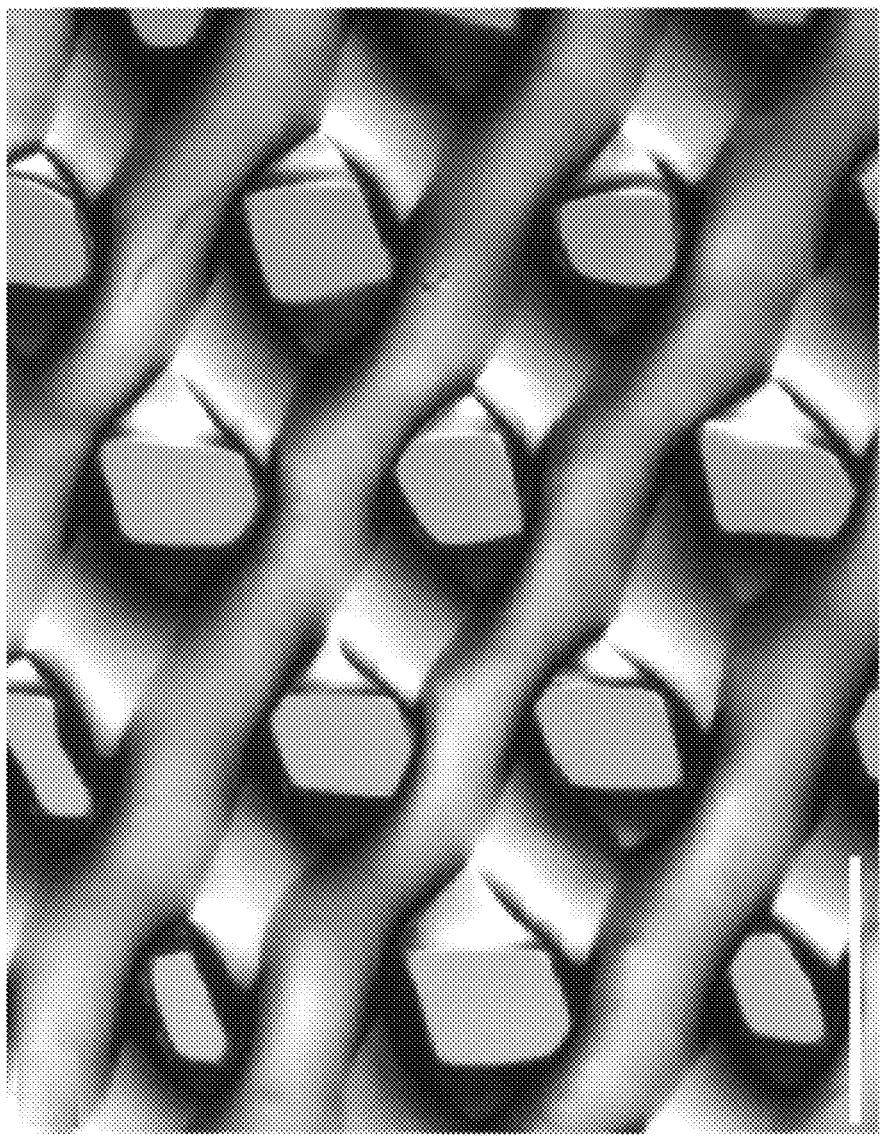
FIG. 6. Image of a 15×15 mm square printed from a PEG-gelatin bioink, 4 layers, scale bar 1 mm.
Figure 7:
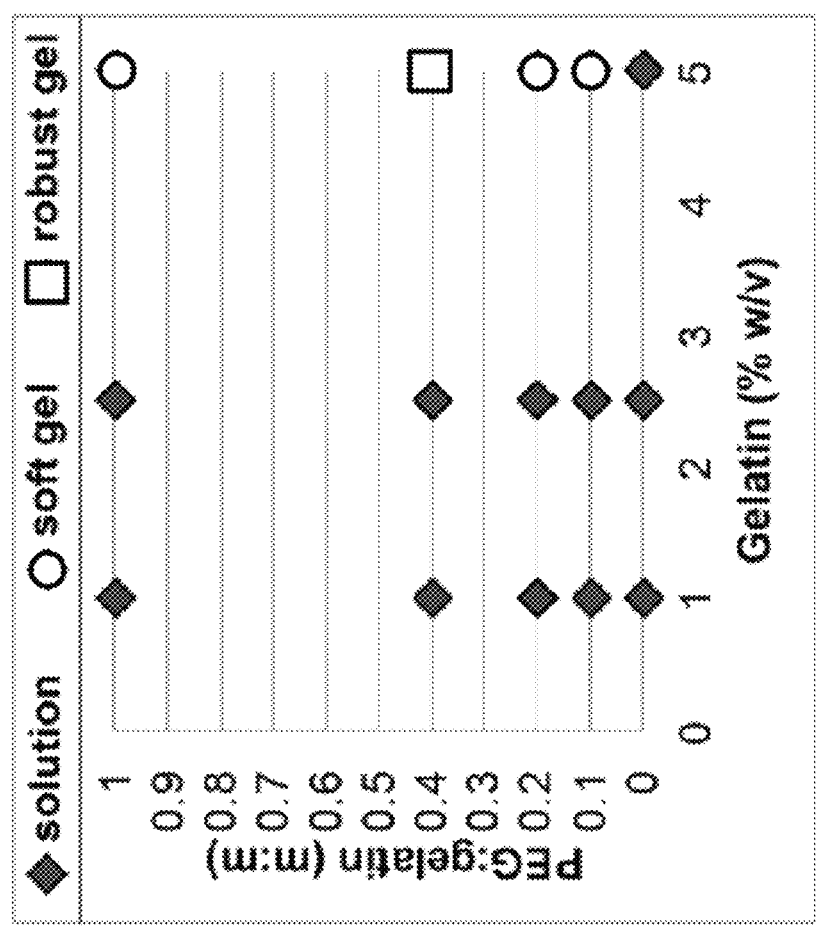
FIG. 7. Phase plot of a bioink comprising gelatin and 1000 g/mol homobifunctional PEG SVA cross-linker.
Figure 8:
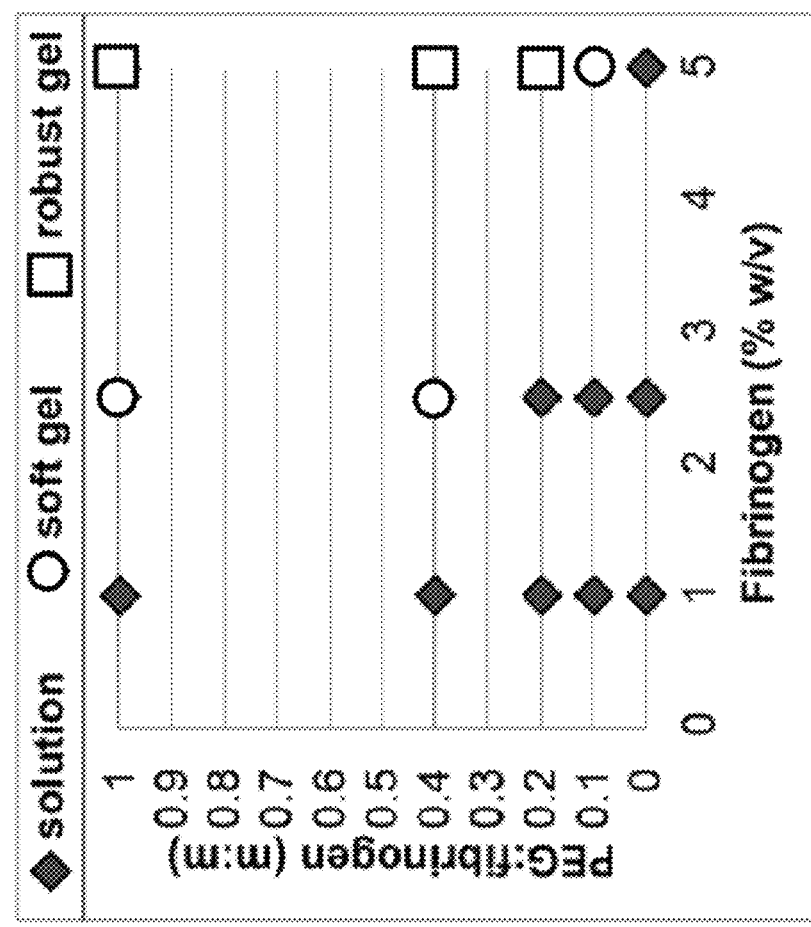
FIG. 8. Phase plot of a bioink comprising fibrinogen and 5000 g/mol homobifunctional PEG SVA cross-linker.

Several candidate bioinks from phase plots were then 3D printed on the EnvisionTEC 3D-Bioplotter® with pneumatically driven extrusion. 5 w/v % gelatin at 0.1 PEG ratio extruded as cohesive filaments of gel through a 200 μm tip. When extruded, gel filaments retained as-printed diameter, allowing printed internal structures to be maintained (FIG. 6). Furthermore, these bioinks exhibited the ability to support the printing of many subsequent layers to create well-defined, thick 3D printed objects. A 20 layer object was produced yielding a ~5 mm thick construct. This ability to create much thicker 3D printed gel scaffolds while preserving the designed internal architecture is an absolute requirement for 3D printing functional tissues and organs with open spaces for nutrient diffusion and vascularization. To probe the versatility of this method, 1000 g/mol homobifunctional PEG SVA was examined and similar soft, spreadable gel characteristics were observed (FIG. 7). This illustrates the ability to employ other physical and chemical PEG variants that can permit a range of new materials and resulting material properties through different cross-linking chemistries. The method was also extended to an additional precursor solution, fibrinogen. Soft gels were observed in these formulations using similar PEG ratios to those found suitable for gelatin and were successfully 3D printed. The PEG-fibrinogen gels and PEG-gelatin gels held their extruded filament shape and supported subsequent printed layers. However, structures printed with these bioinks were not robust enough to be easily handled. To tailor the rigidity and degradation, a secondary, post-printing cross-linking step can be utilized. For example, PEG-fibrinogen printed constructs were further cross-linked by treating with a thrombin-$Ca^{2+}$ solution. The thrombin-treated PEG-fibrinogen strands became opaque and significantly more robust, as well as exhibited a fibrous structure indicative of fibrin assembly. FIG. 8 shows the phase plot of a bioink comprising fibrinogen and 5000 g/mol homobifunctional PEG SVA crosslinker.

PEG-fibrinogen and PEG-gelatin bioinks were successfully co-printed to demonstrate the ability to spatially organize multiple types of extracellular matrix materials in one 3D construct. Extension of this method to another precursor solution shows that this PEG cross-linking bioink method may be utilized as a single platform for multi-extracellular matrix printing, yielding heterogeneous structures more mimetic of natural tissue.

To examine biological compatibility of PEG cross-linked bioinks, cells were mixed within bioink formulations of PEG-gelatin and PEG-fibrinogen at 2E6 cells/mL and subsequently printed. The ink method supported viability of human dermal fibroblasts (HDFs) and human umbilical vein endothelial cells (HUVECs) one day post-printing. Untreated PEG cross-linked bioinks degraded within two days of culture, and thus later time points were not able to be studied. This necessitated post-printing stabilization by a secondary cross-linking step. 3D printed PEG-fibrinogen scaffolds were therefore treated with thrombin for stabilization, and cell viability was confirmed at day 5. These results validate the use of a cell compatible post-printing cross-linking step to tailor the degradation properties of these 3D printed hydrogel scaffolds.

The ability to spatially organize two cell types within the same printed construct was examined. HUVECs stained with CellTracker™ Red were encapsulated in PEG-gelatin bioink and printed into 15×15 mm, 4 layer structures. Human mesenchymal stem cells (hMSCs) stained with CellTracker™ Green were subsequently seeded onto printed cell-laden constructs to fill the open spaces of the internal structure. At four days, hMSCs began to migrate and completely fill the open spaces of the construct and were spread onto the printed filaments. Interestingly, the addition of hMSCs slowed the degradation of the construct. This illustrates the ability to investigate new spatial organizations of cells to understand cell-cell signaling in 3D, which is significant to engineer functional and more complex multi-tissue and organ structures.

In conclusion, these examples illustrate the use of tunable bioinks to create printable gels by incorporating small additions of a PEG cross-linker. These gels extrude through fine diameter nozzles (200 µm) as continuous and cohesive filaments and are self-supporting to build structures layer-by-layer, including thick constructs (>5 mm). The bioinks in these studies yielded at remarkably high strains up to 2000% and possess critical stresses below 2200 Pa. The bioinks can comprise multiple types of extracellular matrix materials, different PEG variants, as well as varying concentrations of the matrix components. Furthermore, good cell viability post-printing was demonstrated, as well as the ability to spatially organize cells within the resulting 3D printed constructs. The bioinks can be used to print heterogeneous structures with bioinks of varying cells and extracellular matrix materials and can provide a more mimetic natural tissue structure for 3D printing of functional tissues and organs.

EXPERIMENTAL SECTION

Bioink Preparation:
Concentrated solutions of hydrogel precursor were prepared at 10 w/v % of either gelatin or fibrinogen (Sigma) at 37° C. Homobifunctional PEG SVA (5000 g/mol or 1000 g/mol, Laysan Bio) was dissolved and concentrated in pre-warmed phosphate-buffered saline solution (PBS) just prior to ink preparation. Cells were concentrated in PBS. Hydrogel precursor polymer solution, PEG cross-linker, PBS (as needed), and cells (optional) were thoroughly mixed, immediately transferred to a glass vial, syringe, or printing cartridge, and held at 37° C. for 1-2 hours. Unless otherwise stated, 5000 g/mol PEG was used.

Phase Plots:
Prepared bioinks were in glass vials. At 120 minutes, vials were inverted to determine if the bioinks had formed a solution or gel phase. Gels were manipulated with a spatula and if they could be spread on the glass vial wall, the gel was designated "soft". If the gel retained its shape, it was designated "robust". Soft gels became candidate inks for printing.

TNBS Assay:
TNBS assay to determine percent reacted amines was performed according to previously published studies. (See, A. F. S. A. Habeeb, *Anal. Biochem.* 1966, 14. 328 and A. J. Kuijpers, H. M. Engbers, J. Krijgsveld, S. A. J. Zaat, J. Dankert, J. Feijen. *J. Biomater. Sci. Polym. Ed.* 2000, 11, 225.) Briefly, after 120 minutes, gels were incubated with TNBS solution (0.01 M in sodium bicarbonate buffer) for 2 hours at 40° C. The gels were then treated HCl (1 M) and SDS (10%) to stop TNBS reaction and dissolve gel for 2 hours at 40° C. Solutions were diluted and absorbance at 340 nm was read on a SpectraMax M5 microplate reader.

Rheology:
Testing was performed using an Anton-Paar MCR 302 rheometer with a cone-plate fixture. Temperature was controlled at 37° C. during testing. Formulations were prepared as above immediately prior to testing, loaded on the warmed plate and the measuring cone was lowered into position. After applying mineral oil to the edges of the fixture to prevent dehydration, a time sweep was performed for 120 min, followed by a frequency sweep and then two amplitude sweeps, using testing parameters described in the text.

Printing:
Bioinks were prepared in a conical tube and quickly transferred to EnvisionTEC high temperature cartridges. The cartridges were stored in a cell culture incubator or within the printing magazine to maintain 37° C. At 1-2 hours, a printing nozzle (200 µm) was fixed onto the cartridge, and gels were printed on the EnvisionTEC 3D-Bioplotter®. Printing pressures and speeds were changed depending on ink flow properties. Gels were typically printed by applying a pressure of 1-2.5 bar at a printing speed of 5 mm/s. Gels were printed onto autoclaved glass slides. Gelatin and fibrinogen co-printed inks were mixed with red and blue food coloring respectively for visualization.

Cell Studies:

P4-P6 human dermal fibroblasts (Cell Applications, Inc.) and human umbilical vein endothelial cells (Lonza Inc.) were incorporated into 5 w/v % gelatin or 3 w/v % fibrinogen at PEG ratios of 0.1 and 0.2 respectively. Fibrinogen printed samples were treated post-printing with 10 U/mL thrombin (Sigma) in 40 mM $CaCl_2$ solution for ~30 minutes. Cell viability was assessed with the Live/Dead® assay (Life Technologies) according to manufacturer's instructions. P4-P6 bone marrow-derived human mesenchymal stem cells (Lonza, Inc.) were seeded onto HUVEC encapsulated PEG-gelatin printed constructs. HUVECs and hMSCs were labeled with CellTracker™ Red (Molecular Probes®) and CellTracker™ Green, respectively according to manufacturer's instructions. Cells were imaged with a Nikon C2+ confocal and Nikon AZ 100 fluorescent stereoscope.

Imaging:

Printed constructs were photographed with a Canon camera or cell phone camera. Photojojo macro lens was also used for pictures and movies taken with cell phone camera. Printed constructs were also imaged with Leica M205 C stereoscope. Confocal stacks were analyzed with ImageJ software. Thrombin-treated fibrinogen constructs were analyzed with LEO Gemini 1525 after glutaraldehyde fixing, critical point drying, and osmium coating.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of forming a three-dimensional object, the method comprising:
extruding a hydrogel composition having a shear storage modulus of less than 300 Pa through the annulus of a channel, the hydrogel composition comprising: water; a crosslinked biocompatible polymer; and a bioactive factor, cells or a combination thereof, wherein the crosslinks between the biocompatible polymer chains comprise repeating units having the following structure:

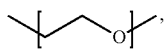

to form a strand comprising a continuous matrix of the biocompatible polymer, wherein the strand substantially retains the three-dimensional shape imparted to it by the extrusion.

2. The method of claim 1, wherein extruding the hydrogel composition through the annulus of a channel comprises printing the hydrogel composition through a printhead nozzle.

3. The method of claim 1, wherein the extruded hydrogel composition comprises reactive functional groups, the method further comprising exposing the extruded hydrogel composition to conditions that induce the reactive functional groups to form additional crosslinks between the biocompatible polymer chains.

4. The method of claim 1, wherein the annulus has a diameter of no greater than 500 μm.

5. The method of claim 1, wherein the annulus has a diameter of no greater than 200 μm.

6. The method of claim 1, wherein the crosslinks are unbranched, linear crosslinks.

7. The method of claim 1, wherein the hydrogel composition has a shear storage modulus in the range from 1 to 150 Pa.

8. The method of claim 1, wherein the hydrogel composition is free of hyaluronic acid.

9. The method of claim 1, wherein the bioactive factors are covalently bound to the crosslinks.

10. The method of claim 1, further comprising forming the hydrogel composition by:
preparing a hydrogel precursor solution comprising water, the biocompatible polymer, a functionalized polyethylene glycol crosslinker, and the bioactive factor, cells or combination thereof, wherein the biocompatible polymer has functional groups capable of undergoing crosslinking reactions with the functionalized polyethylene glycol crosslinker;
inducing the functionalized polyethylene glycol crosslinker to undergo crosslinking reactions with the functional groups on the biocompatible polymer to form the crosslinks between the biocompatible polymer chains; and
allowing the shear storage modulus of the composition to stabilize.

11. The method of claim 10, wherein the functionalized polyethylene glycol crosslinker is a linear bifunctional polyethylene glycol crosslinker.

12. The method of claim 11, wherein the functionalized polyethylene glycol crosslinker is bis-succinimidyl valerate polyethylene glycol.

13. The method of claim 10, wherein the hydrogel precursor solution is free of hyaluronic acid.

14. The method of claim 10, wherein the hydrogel precursor solution has a polymer concentration of less than 5 weight percent.

15. The method of claim 10, further comprising preparing the hydrogel precursor solution by mixing a first solution comprising the biocompatible polymer with a second solution comprising the functionalized polyethylene glycol crosslinking, wherein the first solution has viscosity in the range from about 1 to about 1000 cP.

16. The method of claim 10, wherein the biocompatible polymer comprises a second set of reactive functional groups that differ from the functional groups capable of undergoing crosslinking reactions with the functionalized polyethylene glycol crosslinker, the method further comprising exposing the extruded hydrogel to conditions that induce the second set of reactive functional groups to form additional crosslinks between the biocompatible polymer chains.

17. The method of claim 10, wherein the mass ratio of the functionalized polyethylene glycol crosslinker to the biocompatible polymer in the hydrogel precursor solution is in the range from about 0.1 to about 1 and the molecular weight average molecular weight of the functionalized polyethylene glycol crosslinker is in the range from about 0.5 to 6 k.

18. The method of claim 1, wherein the biocompatible polymer comprises a polymer of amino acids.

19. The method of claim 1, wherein the biocompatible polymer comprises gelatin.

20. The method of claim 1, wherein the shape and structural integrity of the strand is not maintained by a supporting structure or matrix.

* * * * *